(12) United States Patent
Nagano

(10) Patent No.: US 6,376,703 B1
(45) Date of Patent: Apr. 23, 2002

(54) METHOD FOR HANDLING ALKYLAMINO (METH) ACRYLATE AND APPARATUS FOR STORAGE

(75) Inventor: Hideaki Nagano, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/379,068

(22) Filed: Aug. 23, 1999

(30) Foreign Application Priority Data

Aug. 24, 1998 (JP) .......................................... 10-237355
Aug. 24, 1998 (JP) .......................................... 10-237356
Aug. 10, 1999 (JP) .......................................... 11-226968

(51) Int. Cl.$^7$ ...................... C07C 69/52; C07C 261/00; C07C 69/00
(52) U.S. Cl. ...................... 560/205; 560/205; 560/157; 560/4
(58) Field of Search ................................ 560/205, 157; 560/4; 266/90, 121

(56) References Cited

U.S. PATENT DOCUMENTS 4,049,895 A * 9/1977 McOnie et al.
5,466,510 A * 11/1995 Oikawa et al.

FOREIGN PATENT DOCUMENTS

| JP | 53-144521 | 12/1978 | .......... C07C/93/193 |
| JP | 04-134053 | 5/1992 | .......... C07C/219/08 |
| JP | 10-182569 | 7/1998 | .......... C07C/219/08 |

OTHER PUBLICATIONS

Aldrich, Catalog Handbook of Fine Chemicals; P.O.Box 2060, Milwaukee, WI 53201, USA.*

* cited by examiner

*Primary Examiner*—Gary Geist
*Assistant Examiner*—Farhad Forohar
(74) *Attorney, Agent, or Firm*—Fish & Richardson P.C.

(57) ABSTRACT

The storage of alkylaminoalkyl (meth)acrylate is made in a container made of stainless steel whose wall surface has not more than 1.6 μm for the Ra defined in JIS B 0601. And the compound is stored in a container having a water concentration of not more than 0.1 vol. % and a molecular oxygen concentration exceeding 0 to 10 vol. % in the gas phase part of the container.

When the compound is handled under these conditions, it is enabled to retain the (meth)acrylic acid concentration therein below 0.1 wt. %, prevented from producing a polymer or a precipitate, and precluded from coloration.

18 Claims, 1 Drawing Sheet

APPARATUS For DAA STORAGE

METHOD FOR HANDLING ALKYLAMINO (METH) ACRYLATE AND APPARATUS FOR STORAGE

BACKGROUND OF THE INVENTION

1. Field of the Invention

This invention relates to a method for handling such alkylaminoalkyl (meth)acrylates as dimethylaminoethyl acrylate, diethylaminoethyl acrylate, and dimethylaminoethyl methacrylate as during storage, transport, transfer, haulage etc. and a method for preventing them from coloration.

2. Description of Related Art

Alkylaminoalkyl (meth)acrylates are useful as a dye-affinity improver for fibers, an antistatic agent for plastics, a pigment dispersant for coating materials, an ultraviolet-curing auxiliary etc. and are used in the form of varying kinds of derivatives as produced by quaternization of amino groups. In addition thereto, the derivatives producing by homopolymerization thereof or copolymerization thereof with an unsaturated compound are used as a fiber treating agent, a toner binder, a coating material, a lubricant additive, an adhesive agent, an ion-exchange resin, a cationic macromolecular flocculant etc. and are finding utility in a wide range of applications.

Since such an alkylaminoalkyl (meth)acrylate contains a double bond, an ester moiety, and an amino group in the molecular unit thereof, it abounds exceptionally in reactivity and, at the same time, suffers excessive unsteadiness. When this compound is put to storage, therefore, it at once yields to coloration and gives rise to a polymer and this trend gains in severity with time. When the discolored alkylaminoalkyl (meth)acrylate is used in manufacture, the secondary product consequently obtained is also discolored. The desirability of preventing this compound from this coloration and enabling it to acquire stability, therefore, has been finding unusually enthusiastic recognition.

A example cited in JP-A-04-169,559, for example, disclosed the effect that the coloration of an alkylaminoalkyl (meth)acrylate does not advance so much when it is stored in a glass container as when it is stored in a container made of stainless steel (SUS 304). The storage in glass containers, however, boosts the cost of equipment on a commercial scale. The glass containers are at a disadvantage in being deficient in strength and difficulty to manufacture in large sizes as compared with metallic containers, heavy, and inconvenient to handle. Though containers whose interior are coated with chemically inactive fluorine resin are usable for storing the compound under discussion, they are deficient in service durability.

Concerning the storage of an alkylaminoalkyl (meth) acrylate, JP-A-04-134,054 and JP-A-04-169,559 disclosed the effect that the coloration of an alkylaminoalkyl (meth) acrylate is allayed when the compound is stored in an atmosphere having no oxygen content or an atmosphere having only a low oxygen content. The methods of storage disclosed by these patent publications, however, incur a high cost of electric power because they require to use electric power for lowering the concentration of oxygen or the temperature of conservation. This storage is practicable in a stationary storage container. When it is applied to such transportable containers as shipping containers and tank lorries, however, it has the problem of operational inefficiency because these containers assume an atmosphere of air whenever they are packed with a load and they consequently require to lower the oxygen concentration of the load.

The patent publications also disclosed the effect that the coloration of the alkylaminoalkyl (meth)acrylate does not proceed when the compound is stored at a low temperature of not higher than 5° C. From the viewpoint of securing stability, however, the alkylaminoalkyl (meth)acrylate is preferably transported at a low temperature of not higher than 5° C. The use of the low temperature, however, is at a disadvantage in adding to the cost of transportation. Moreover, in terms of handling, even the normal temperature proves advantageous for the transportation so long as it enables the compound to secure stability enough to prevent coloration and polymerization.

JP-A-04-134,053 mentioned above discloses a method which has recourse to the addition of hydroquinone monomethyl ether in combination with the presence of oxygen. Even when the alkylaminoalkyl (meth)acrylate is stored in the conditions proposed thereby, it possibly generates a while precipitate, stains the container used for storage or transportation, and blocks pipings for a cause yet unknown.

The addition of a stabilizer for the purpose of preventing polymerization has been studied in connection with the method for storage of alkylaminoalkyl (meth)acrylate. JP-A-53-144,521, for example, discloses a method for preventing N,N-dimethylaminoethyl acrylate from polymerization and coloration during storage by the use of phenothiazine. The addition of such a polymerization inhibitor, however, brings no decrease in the white precipitate. JP-A-10-182,569 discloses a method which, for the purpose of stabilizing in color, comprises in handling the compound with a phenolic compound in the presence of at least one member selected from the group consisting of amid group-containing compounds, phosphorous esters, phosphoric esters, and phosphines. The use of the new additive results in boosting the cost of storage.

SUMMARY OF THE INVENTION

This invention is aimed at preventing an alkylaminoalkyl (meth) acrylate in storage from succumbing to coloration, giving birth to a precipitate, and yielding to polymerization.

Specifically, this invention concerns a method for handling an alkylaminoalkyl (meth)acrylate represented by the general formula (1)

(1)

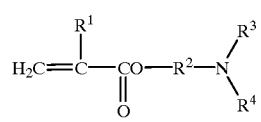

(wherein $R^1$ represents a hydrogen atom or a methyl group, $R^2$ an alkylene group of 1–4 carbon atoms, $R^3$ a hydrogen atom or an alkyl group of 1–8 carbon atoms, and $R^4$ an alkyl group of 1–8 carbon atoms) by keeping in contact with stainless steel, wherein said stainless steel contacting with said compound is not more than 1.6 μm for the Ra defined in JIS (Japanese Industrial Standard) B 0601.

Further, this invention concerns a method for handling an alkylaminoalkyl (meth)acrylate represented by the general formula (1)

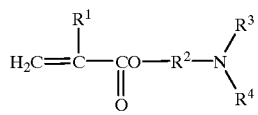

(1)

(wherein R¹ represents a hydrogen atom or a methyl group, R² an alkylene group of 1–4 carbon atoms, R³ a hydrogen atom or an alkyl group of 1–8 carbon atoms, and R⁴ an alkyl group of 1–8 carbon atoms), wherein the water concentration is not more than 0.1% based on the volume of gas phase part contacting with said compound and concentration of (meth)acrylic acid is not more than 0.1% based on the weight of said allkylaminoalkyl (meth)acrylate.

This invention also concerns a method for preventing alkylaminoalkyl (meth)acrylate represented by the general formula (1)

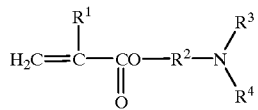

(1)

(wherein R¹ represents a hydrogen atom or a methyl group, R² an alkylene group of 1–4 carbon atoms, R³ a hydrogen atom or an alkyl group of 1–8 carbon atoms, and R⁴ an alkyl group of 1–8 carbon atoms) from coloration by keeping in contact with stainless steel, wherein said stainless steel contacting with said compound is not more than 1.6 μm for the Ra defined in JIS (Japanese Industrial Standard) B 0601.

Besides, this invention concerns a method for preventing alkylaminoalkyl (meth)acrylate represented by the general formula (1)

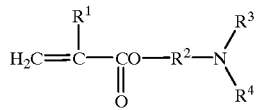

(1)

(wherein R¹ represents a hydrogen atom or a methyl group, R² an alkylene group of 1–4 carbon atoms, R³ a hydrogen atom or an alkyl group of 1–8 carbon atoms, and R⁴ an alkyl group of 1–8 carbon atoms) from coloration, wherein the water concentration is not more than 0.1% based on the volume of gas phase part contacting with said compound and concentration of (meth)acrylic acid is not more than 0.1% based on the weight of said alkylaminoalkyl (meth) acrylate.

Further, this invention is directed at providing an apparatus to use for the method according to Item 1, which comprises a container made of stainless steel whose wall surface contacting with said compound is not more than 1.6 μm for the Ra defined in JIS B 0601 and means for retaining the water content in the gas phase part of a storage container below 0.1 vol. %.

DESCRIPTION OF PREFERRED EMBODIMENT

Figure 1:
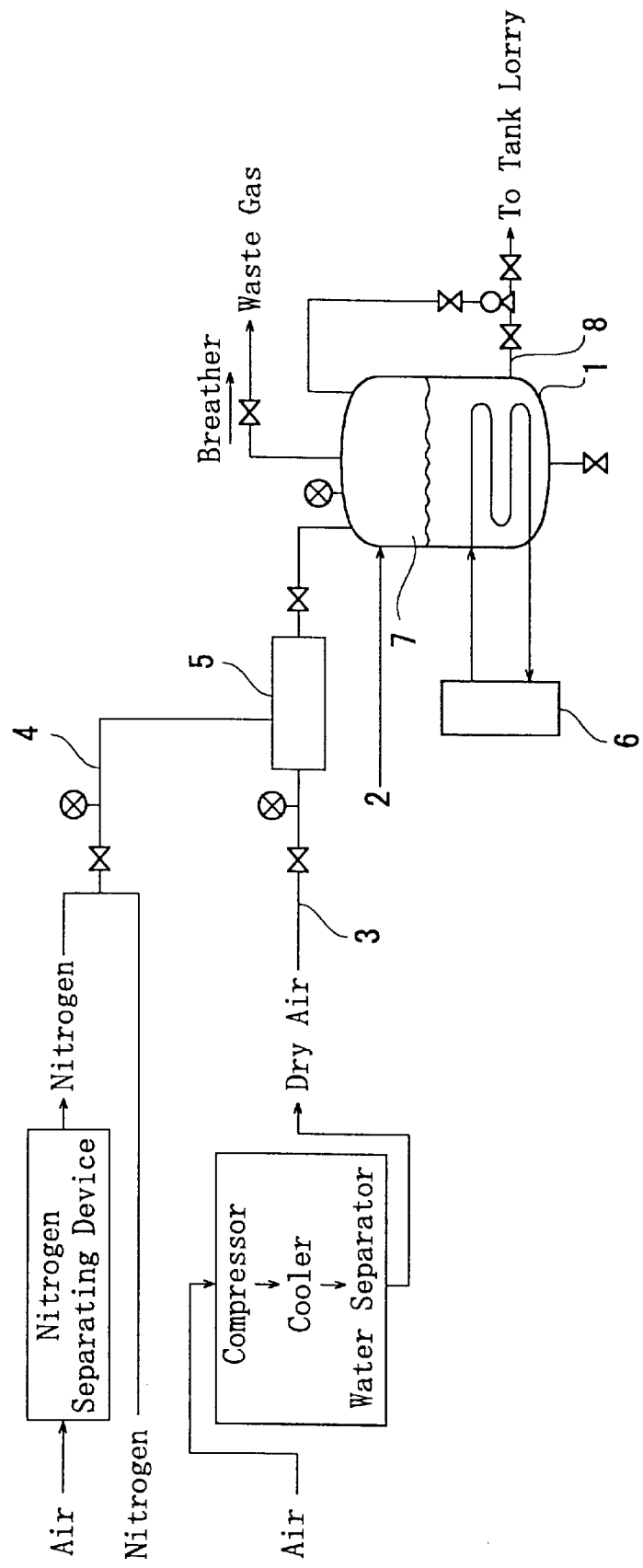
FIG. 1 is a diagram schematically illustrating an apparatus of this invention for storage of an alkylaminoalkyl (meth) acrylate.

This invention, by giving a surface smoothness, Ra, of not more than 1.6 μm to the interior of stainless steel contacting with an alkylaminoalkyl (meth)acrylate, represses coloration of the alkylaminoalkyl (meth)acrylate even under such a condition of conservation as 40° C., allows the gas phase part of the container to remain in an atmosphere having a specific water concentration, and prevents the compound from succumbing to polymerization and consequently giving birth to a precipitate.

Though the mechanism for the coloration of the alkylaminoalkyl_(meth)acrylate remains yet to be elucidated in detail, the coloration may be explained by that the oxygen acts to generate a radical and the iron contained in the reaction vessel functions as a catalyst for promoting an oxidation reaction and inducing the coloration of the compound held in the vessel. A method for preventing polymerization by mingling an oxygen gas into an atmosphere of an easily polymerizing substance has been known to the art. When the oxygen gas is used, however, the prevention of coloration is not attained because the oxidation reaction is promoted. The present invention is capable of preventing coloration very effectively by using a container which has not more than 1.6 μm for the Ra of the wall face thereof. Moreover, the very effective prevention of coloration is attained even when the compound is stored in the container made of an iron-containing substance such as stainless steel. Heretofore, a method for storing the easily polymerizing substance in a container having undergone an electrolytic complex grinding treatment for the purpose of repressing polymerization has been known. It has never been known the fact that the effect of preventing a content from coloration is achieved by using a container having a smooth wall surface.

This invention further is capable of precluding occurrence of a precipitate and repressing polymerization and coloration by lowering the water concentration in the gas phase part of the container during the storage of the alkylaminoalkyl (meth)acrylate. Now, this invention will be described in detail below.

As concrete examples of the alkylaminoalkyl (meth) acrylate which is represented by the general formula (1) in this invention, N,N-dimethylaminoethyl acrylate, N,N-diethylaminoethyl acrylate, N,N-dipropylaminoethyl acrylate, N,N-dibutylaminoethyl acrylate, N,N-dimethylaminopropyl acrylate, N,N-diethylaminopropyl acrylate, N,N-dipropylaminopropyl acrylate, N,N-dibutylaminopropyl acrylate, N,N-dimethyl-aminoethyl methacrylate, N,N-diethylaminoethyl methacrylate, N,N-dipropylaminoethyl methacrylate, N,N-dibutylaminoethyl methacrylate, N,N-dimethylaminopropyl methacrylate, N,N-diethyl aminopropyl methacrylate, N,N-dipropylaminopropyl methacrylate, and N,N-dibutylaminopropyl methacrylate may be cited. This invention allows these compounds to be used not only singly but also in the form of two or more members.

This invention is characterized in that the stainless steel has such a surface smoothness on the wall contacting with the compound has the arithmetical mean deviation of profile (Ra) defined in JIS B 0601 (1982) of not more than 1.6 μm. The reason for using a container having such an Ra value is that the container, even when it is made of such an iron-containing substance as stainless steel, can prevent the compound from coloration very effectively. It is suspected that in the reaction vessel having an convexoconcave in the wall surface, the oxidation reaction is promoted because the content is suffered to collide violently against itself but that in the reaction vessel having a smooth surface, the oxidation reaction is repressed. As a result, by preservation of the easily polymerizing substance in such container the coloration based on the oxidation reaction can be prevented and at the same time, the polymerization reaction of the compound can be controlled as well.

The term "arithmetical mean deviation of profile (Ra) in the center line" mentioned above is based on the specification of JIS B 0601-1982. Specifically, it is found by extracting a portion of measurement length L on the center line for a given roughness curve, expressing the center line of the extracted portion as X axis, the direction of the longitudinal magnification as Y axis, and the roughness course as y=f(x), calculating the following formula using these values, and reporting the outcome of this calculation on the denomination of micrometer ($\mu$m). This measurement of the value of Ra can be carried out by using a stylus surface roughness meter (JIS B 0651), a light wave interference type surface roughness meter (JIS B 0652) etc.

$$Ra = \frac{1}{l}\int_0^l |f(x)|dx$$

For this invention, the Ra value is only required to be not more than 1.6 $\mu$m, preferably to fall in the range of 0.8–0.001 $\mu$m, and more preferably to fall in the range of 0.2–0.001 $\mu$m. The reason for these specific limits is that the alkylaminoalkyl (meth)acrylate is discolored during the course of storage and transportation when the Ra value exceeds 1.6 $\mu$m and that the Ra value below 0.001 $\mu$m is obtained with difficulty.

The kind of stainless steel to be used for containing the alkylaminoalkyl_(meth)acrylate may be any of the so-called austenitic, martensitic type, and ferritic stainless steel. From the ease of procurement and fabrication, it is preferable to use an austenitic stainless steel such as SUS-304 or SUS-316.

To acquire the Ra value mentioned above, any of the known means of polishing may be used. For example, the mechanical polishing represented by the buffing, the electrolytic polishing methods which are capable of smoothing surface to a still higher level, and the complex electrolytic polishing are available.

The buffing is a polishing method which is used mainly for obtaining a smooth surface or a glossy surface. The coarse polishing by the use of a stationary abradant, the intermediate polishing by the use of a semisolid or free abradant, and the finish polishing may be adopted therefor. Besides such soft materials as leather and fabric, the buffing abradants may embrace oleosus and fatty, nonloeosus and fatty abradant and the abradent used by spray which is containing tripoli silica stone, chromium oxide, silicon carbide, fused alumina, calcined alumina, and chromium oxide may be used.

The electrolytic polishing is a method for smoothing a metal surface meanwhile dissolving the surface layer thereof. As the electrolytic abradant solution for the container of stainless steel, perchloritic acid type, sulfuric acid type, phosphoric acid type, and sulfuric acid-phosphoric acid type solutions can be used. The electrolytic abradant can be properly selected to suit the composition of the container to be used because the stainless steel has the texture thereof largely varied not merely by the difference of the composition of the container to be used but also by the degree of heat treatment and fabrication. Such factors that the amount of the acetic anhydrous to be generally applied to the electrolyte of a hydrochloric acid type such as, for example, the electrolyzing temperature, the current density, and the electrolyzing time, therefore, may be properly selected. Optionally, the composite electrolytic polishing which further performs an electrolytic polishing treatment subsequent to the mechanical publishing may be adopted.

For this invention, it is most preferable to perform the complex electrolytic polishing. It can be accomplished, for example, by a method which uses an aqueous neutral salts solution as the electrolyte and effects the polishing by incorporating a proper abrasive grain in the aqueous solution and pressing the aqueous solution against a surface to be polished. Then, by forming an immobilized coating electrolytically on the concavoconvex of the surface to be polished and forcibly removing the convex from the surface by virtue of the abrading force of the abradant or abrasive grains, the speed of polishing can be improved and the surface can be finished in specular fineness. By this complex electrolytic polishing, the Ra value can be easily adjusted to fall in the range of 0.01–0.1.

The container of stainless steel to be used in handling the alkylaminoalkyl (meth)acrylate according to this invention is proper to have a water concentration of not more than 0.1 vol. % in the gas phase part of the container. This water concentration is preferably in the range of 0.000001–0.015 vol. %, and more preferably in the range of 0.00001–0.005 vol. %. Since the alkylaminoalkyl (meth)acrylate has an ester moiety in the structure thereof, it is liable to release (meth)acrylic acid when it is hydrolysed. The amount of water in the gas phase part is decreased, therefore, by repressing this decomposition. For the unknown cause, the compound being handled generates a precipitate when the water content exceeds 0.1 vol. %. Though the water content is preferred to be as small as possible, the effort to limit it below 0.000001 vol. % is expensive and impracticable from the technical and economic points of view. By adjusting the water content in the range mentioned above, therefore, the formation of acrylic acid as a product of decomposition can be repressed and the coloration and the precipitation of an alkylaminoallkyl (meth)acrylate due to the presence of the acid component can be further repressed.

In this invention, the oxygen concentration is preferred not less than 0 to 10 vol. % of the gas phase part contacting with the compound. When the conservation of the compound is made under the condition purged of oxygen gas, the coloration can be prevented because the oxidation reaction can be repressed. On the other hand, the oxygen gas is also a substance which represses polymerization of an easily polymerizing substance. So, the condition which is devoid of oxygen gas brings a contradiction of giving rise to a polymer of the compound during storage. This invention can repress the coloration very effectively even under the condition allowing the presence of molecular oxygen in a prescribed range.

In this invention, the molecular oxygen concentration is properly not less than 0 to 10 vol. %, preferably in the range of 0.01–10 vol. %, more preferably in the range of 0.05–7 vol. %, and particularly preferably in the range of 0.1–5 vol. %. The reason for the specific range is that the possibility of polymerization will ensue if the oxygen concentration is lower than 0.01 vol. % and that the alkylaminoalkyl (meth) acrylate will tend to discolor if the oxygen concentration exceeds 10 vol. %.

The adjustment of the molecular oxygen concentration to the range of 0.01–10 vol. % may be attained by a method which consists in diluting the air or oxygen with an inert gas. As concrete examples of the inert gas, nitrogen, helium, argon etc. may be cited. Particularly, the molecular oxygen-containing gas obtained by diluting air with nitrogen is advantageous because it is inexpensive and easy to handle.

Likewise, the adjustment of the water concentration of the gas phase part to below 0.1 vol. % is achieved by adopting any of the methods known to the art. For example, a method which constantly blows the molecular oxygen-containing gas having the water concentration adjusted to below 0.1 vol. % into the gas phase part of the container storing the alkylaminoalkyl (meth)acrylate, a method which blows the gas when it is extracted from the container having stored the gas, or a method which introduces the ambient air of the container into the container after it has been passed through a dehydrating agent such as silica gel or calcium chloride during the extraction from the container which has been used for storage may be adopted. Further, the adjustment of the water content of the molecular oxygen-containing gas to below 0.1 vol. % may be effected by adopting any of the methods shown to the art. For example, a method which removes the water content by cooling the molecular oxygen-containing gas to below −20° C., a method which removes the water content by cooling air or oxygen to below −20° C. and then dilutes the air or oxygen with inert gas deprived similarly of the water content, or a method which passes the molecular oxygen-containing gas through a dehydrating agent such as silica gel or calcium chloride may be adopted. During the term of storage, the dissolved oxygen in the alkylaminoalkyl (meth)acrylate possibly decreases with time. It is suspected that this decrease occurs because the dissolved oxygen reacts with the allkylaminoalkyl (meth) acrylate. During the long-term storage, therefore, it is preferred to retain this concentration by suitably supplying oxygen.

This invention is further characterized by retaining the (meth)acrylic acid concentration in the alkylaminoalkyl (meth)acrylate to below 0.1 wt. %. The increase of (meth) acrylate in the alkyl-amino(meth)acrylate is caused by the hydrolysis of the alkylaminoalkyl (meth)acrylate. For the purpose of repressing the hydrolysis, it is necessary to avoid contact between the alkylaminoalkyl (meth)acrylate and water to the fullest possible extent. The avoidance of the water content may be attained by adopting any of the various known methods described above. Further, a method which thoroughly dries the container to be handled and then puts it to use, a method adds a water removing agent such as molecular sieve or magnesium sulfate to the interior of the container, a method which lowers the water concentration in the gas phase part to below 0.1 vol. % for the purpose of repressing the absorption of water from the gas phase part, a method which floats a gas barrier film in the interface between the alkylaminoalkyl (meth)acrylate and the gas phase, or a method which floats an oil causes no solution with the alkylaminoalkyl (meth)acrylate and fates to form an upper layer when two-phase separation occurs may be adopted.

In this invention, the storage temperature during the handling of the alkylaminoalkyl (meth)acrylate is not higher than 40° C. and is preferably in the range of −20° C.–30° C., more preferably in the range of 0° C.–25° C., and further preferably in the range of 0° C.–20° C. If the liquid temperature exceeds 40° C., the alkylaminoalkyl (meth) acrylate will tend to discolor. If this temperature is lower than −20° C., it will be at a disadvantage in suffering the gas phase part to condensate in a gas having a water content of 0.1 vol. % and the resultant water drops to mingle into the alkylaminoalkyl (meth)acrylate. A still lower temperature is expensive and impracticable from the commercial point of view.

From the viewpoint of securing stability inherent in a substance, the temperature of conversation is preferred to be as low as permissible. The constant retention of a low temperature, however, is inconvenient in terms of handling. Since the present invention represses the reaction of polymerization and the reaction of coloration by adopting the Ra value to the wall surface of the container described above, it can secure very fine stability of the alkylaminoalkyl (meth)acrylate and consequently can repress the reaction of polymerization, the reaction of coloration, and the reaction of precipitation in spite of such a high temperature as 40° C. as demonstrated in the working examples to be cited herein below.

Generally, the alkylaminoalkyl (meth)acrylate often incorporates therein a polymerization inhibitor for the purpose of repressing polymerization during storage. This invention may contemplate this incorporation of the polymerization inhibitor for the sake of ensuring prevention of polymerization.

The polymerization inhibitor to be used herein may be any of the compounds known to the art. As concrete examples of the polymerization inhibitor, amide group-containing compounds such as hydroquinone monomethyl ether, methoquinone, cresol, phenol, t-butyl catechol, diphenyl amine, phenothiazine, di-t-butylcatechol, cupferron, and 2,2-oxamide bis-[ethyl-3-(3,5-di-t-butyl-4-hydroxyphenyl) propionate], phosphorous esters such as triphenyl phosphite, tris(nonylphenyl)phosphite, triethyl phosphite, tris (2-ethylhexyl)phosphite, tridecylphosphite, tris(isodecyl) phosphite, and tris(tridecyl)phosphite, phosphate esters such as ethyldiethyl phosphoroacetate, and phosphines such as trimethyl phosphine, triethyl phosphine, tripropyl phosphine, tributyl phosphine, trioctyl phosphine, triphenyl phosphine, and tricyclohexyl phosphine may be cited.

The term "handling" as used in this invention means storage as in a tank, transfer by means of a tank lorry, and conveyance with a pipeline including pipes, valves, and nozzles. In accordance with, the stainless steel which contacts with the alkylaminoalkyl_(meth)acrylate comprises a storage container, pipes and so on made of stainless steel. Since the alkylaminoalkyl (meth)acrylate handled by the method of this invention is not discolored even after long-term storage, the various polymers which are obtained by homopolymerizing this compound or copolymerizing the compound with another copolymerizable monomer quite excel in color characteristics and enjoy high commercial value.

A typical storage device usable by the method of handling the alkylaminoalkyl (meth)acrylate according to this invention is illustrated in FIG. 1.

An alkylaminoalkyl (meth)acrylate as a product is introduced into a storage container (1) having not more than 1.6 μm for Ra of the wall surface of the storage container. Optionally, the product may incorporate in advance therein a polymerization inhibitor. The storage container (1) is provided with a feed inlet (2) and a discharge outlet (8) for the product alkylaminoalkyl (meth)acrylate and is connected to a dry air feed path (3) and an inert gas feed path (4) for adjusting the water content and the oxygen concentration of the gas phase part. The dry air feed path (3) is intended to compress and cool the ambient air and separate the water contained in the ambient air and supply dry air. Any of known means capable of supplying dry air may be adopted as the dry air feed path (3). In this invention, the water content of the dry air is preferably in the range of 0.00000–0.25 vol. %, more preferably in the range of 0.001–0.1 vol. %. The oxygen concentration in the dry air is preferably in the range of −18–22 vol. %, and more preferably in the range of 20–21 vol. %.

The inert gas feed path (4) is intended to supply the inert gas to be mixed with the dry air discharged from the dry air feed path (3) mentioned above for the purpose of adjusting the oxygen concentration. As the inert gas, the commercially available argon gas or nitrogen gas may be used in its unmodified form. Otherwise, the nitrogen gas separated from the ambient air may be used by itself or as mixed with the gas from an inert gas cylinder. The water content of the gas discharged from the insert gas feed path (4) is preferably in the range of 0.000001–0.2 vol. %, more preferably in the range of 0.001–0.1 vol. %. The oxygen concentration is preferably in the range of 0.00001–0.1 vol. %, more preferably in the range of 0.001–0.01 vol. %.

In this invention, a gas mixing part (5) serves the purpose of mixing the gas from the dry air feed path (3) with the gas supplied from the inert gas feed path (4) and introducing the mixed gas into a gas phase part (7) of the storage container (1). The amount of the gas supplied from the dry air feed path (3) and the amount of the gas from the inert gas feed path (4) are adjusted so as to control the water content in the gas mixing part at a level of not more than 0.1 vol. % and the oxygen concentration at a level in the range of 0 to 10 vol. %. Since the water content in the gas phase part is varied by the water content of the product introduced into the storage container (1), the amounts of gases supplied from (3) and (4) may be altered by the known technique in conformity with the changes in the water content and the oxygen concentration of the gas phase part.

This invention optionally provides the storage container with a heat exchanger. The adjustment of the temperature of the alkylaminoalkyl (meth)acrylate in storage can be attained, for example, by the method which introduces a condenser tube through a heat exchanger (6) into the container as illustrated in FIG. 1 or by jacketing the storage container.

EFFECTS OF THE INVENTION (1) In accordance with this invention, by adjusting the Ra value of the wall surface of the interior of the storage container, the coloration can be exceptionally effectively repressed even when the storage container in use happens to be made of stainless steel. The repressing effect is excellent even when the storing temperature is 40° C. and the atmosphere of the gas phase is air. This fact means economization of the cooling expense and simplification of the apparatus. Thus, the present invention provides a highly practical method for storage and for prevention of coloration.

(2) The presence of a molecular oxygen-containing gas generally promotes the oxidation reaction. Since this invention is capable of repressing the oxidation reaction and preventing the coloration by using a storage container having 1.6 $\mu$m for the Ra value of the wall surface, it can repress even the polymerization reaction and the gelation of the alkylaminoalkyl (meth)acrylate which occurs in the absence of molecular oxygen. The conventional method has failed to attain thorough prevention of coloration when the molecular oxygen concentration in the gas phase part is 20 vol. %, i.e. the amount of oxygen normally present in the air. According to this invention, coloration, formation of a polymer, and formation of a precipitate can be effectively prevented by fixing the water content and the smoothness of the wall surface of the container in respectively specified ranges.

(3) According to this invention, the hydrolysis of alkylaminoalkyl_(meth)acrylate is inhibited by lowering the water content of the gas phase part and the formation of (meth)acrylic acid as a by-product can be consequently repressed. Since this (meth)acrylic acid is an acidic substance, the presence thereof further promotes secondary reactions. This invention enables the alkylaminoalkyl (meth)acrylate product to retain the purity thereof at a high level by repressing the hydrolysis.

(4) By using the storage container which has 1.6 $\mu$m as the Ra value of the wall surface, the reaction of coloration and the reaction of polymerization can be repressed and, even when a polymerization inhibitor is incorporated, the precipitate which is formed as conventionally experienced owing to the insolubility of the compound can be prevented.

(5) According to this invention, the alkylaminoalkyl (meth)acrylate can be stably stored with a simple device. The storage container is only required to be a product obtained by giving the wall surface of a conventional storage container of stainless steel the Ra value of not more than 1.6 $\mu$m as by means of composite electrolytic polishing. It is, therefore, manufactured easily. Moreover, stainless steel excels in service durability unlike a coating formed with inert resin and exhibits high strength unlike glass. Also in this respect, the device above mentioned is really practical.

(6) Since the present invention permits stable storage of the alkylaminoalkyl (meth)acrylate, the secondary products obtained by using the alkylaminoalkyl (meth)acrylate stored in the container can be prevented from coloration.

(7) When the method of storage according to this invention is used, the alkylaminoalkyl (meth)acrylate can be stably stored for a long time, generally one week or more, sometimes 20 days or more, because the precipitate originating in the alkylaminoalkyl (meth)acrylate is not allowed to occur and polymerization of the alkylaminoalkyl (meth) acrylate can be repressed and the advance of coloration of the alkylaminoalkyl (meth)acrylate can be repressed as well.

(8) When this invention is adopted, the alkylaminoalkyl (meth)acrylate can be stably handled easily for a long time, generally one week or more, sometimes 20 days or more, because the precipitate originating in the alkylaminoalkyl (meth)acrylate is not allowed to occur and polymerization of the alkylaminoalkyl (meth)acrylate is repressed and coloration of the alkylaminoalkyl (meth)acrylate is repressed.

EXPERIMENTS

Now, this invention will be described specifically below with reference to working examples. With respect to the method and the condition of storage, this invention is not limited to these working examples. The (meth)acrylic acid concentration in the alkylaminoalkyl (meth)acrylate indicated in the examples was determined by gas chromatography.

Example 1

In a hermetic glass container (made by Maruemu and sold under the mark designation of "Media Vial T-200A"), 150 ml of dimethylaminoethyl acrylate (of the grade containing 1900 ppm of hydroquinone monomethyl ether and having the initial color tone (APHA) of 5, made by Nippon Shokubai K. K.) was placed. In this container, a test piece (measuring 100 mm in length, 20 mm in width, and 4 mm in thickness) of SUS 304 having the Ra of 0.14 $\mu$m was placed. The upper gas phase of the container was formed of an atmosphere of air (molecular oxygen concentration 21%). The storing temperature was set at 40° C.

After seven days' standing of the test piece at rest, the dimethylaminoethyl acrylate solution was visually examined as to the color tone, the adhesion of polymer, and the precipitate. The results are shown in Table 1.

Examples 2–6

The storage was performed by following the procedure of Example 1 while using the varying conditions shown in Table 1 instead. After seven days' standing at rest, the solutions were visually observed with respect to the color tone, the adhesion of polymer, and the precipitate. The results are shown in Table 1.

Examples 7–9 and Referential Example 1

The storage was performed by following the procedure of Example 1 while using the varying conditions shown in Table 2 instead. After seven days' standing at rest, the solutions were visually observed with respect to the color tone, the adhesion of polymer, and the precipitate. The results are shown in Table 2.

Example 10

In a 200 ml of well closed glass container (made by Maruemu and sold under the mark designation of "Media Vial T-200A"), 200 ml in inner volume, 150 ml of dimethylaminoethyl acrylate (of the grade containing 1900 ppm of hydroquinone monomethyl ether and having the initial color tone (APHA) of 5, made by Nippon Shokubai K. K.) was placed. In this container, a test piece (measuring 100 mm in length, 20 mm in width, and 4 mm in thickness) of SUS 304 having an Ra of 0.14 $\mu$m was placed. The upper gas phase of the container was formed of an atmosphere of air (molecular oxygen concentration 21%). The storing temperature was set at 40° C.

After 28 days' standing of the test piece at rest, the dimethylaminoethyl acrylate solution was visually examined as to the color tone, the adhesion of polymer, and the precipitate. The results are shown in Table 3.

TABLE 1

|  | Example 1 | Example 2 | Example 3 | Example 4 | Example 5 | Example 6 |
|---|---|---|---|---|---|---|
| Ra of test piece of SUS 304 | 0.31 | 0.10 | 1.6 | 0.01 | 0.31 | 0.10 |
| Initial color tone (APHA) | 5 | 5 | 5 | 5 | 5 | 5 |
| Atmosphere of gas phase part | Air | Air | Air | Air | 7% oxygen/nitrogen | 7% oxygen/nitrogen |
| Water content (%) of gas phase part | 0.01 | 0.01 | 0.01 | 0.01 | 0.008 | 0.008 |
| Storing temperature (° C.) | 40 | 40 | 40 | 40 | 40 | 40 |
| Color tone after seven days (APHA) | 100 | 90 | 110 | 80 | 90 | 80 |
| Concentration of acrylic acid (ppm) | 34 | 32 | 33 | 33 | 24 | 24 |
| Precipitate | None | None | None | None | None | None |

TABLE 2

|  | Example 7 | Example 8 | Example 9 | Referential Example 1 |
|---|---|---|---|---|
| Ra of test piece of SUS 304 | 2.11 | 6.43 | 2.11 | None of test piese (glass) |
| Initial color tone (APHA) | 5 | 5 | 5 | 5 |
| Atmosphere of gas phase part | Air | Air | 7% oxygen/nitrogen | Air |
| Water content (%) of gas phase part | 0.01 | 0.01 | 0.008 | 0.01 |
| Storing temperature (° C.) | 40 | 40 | 40 | 40 |
| Color tone after seven days (APHA) | 240 | 280 | 200 | 80 |
| Concentration of acrylic acid (ppm) | 32 | 34 | 24 | 33 |
| Precipitate | None | None | None | None |

Example 11–15

The storage was performed by following the procedure of Example 10 while using the varying conditions shown in Table 3 instead. After 28 days' standing at rest, the solutions were visually observed with respect to the color tone, the adhesion of polymer, and the precipitate. The results are shown in Table 3.

Controls 1–3 and Referential Example 2

The storage was performed by following the procedure of Example 10 while using the varying conditions shown in Table 4 instead. After 28 days' standing at rest, the solutions were visually observed with respect to the color tone, the adhesion of polymer, and the precipitate. The results are shown in Table 4.

TABLE 3

|  | Example 10 | Example 11 | Example 12 | Example 13 | Example 14 | Example 15 |
|---|---|---|---|---|---|---|
| Ra of test piece of SUS 304 | 0.31 | 0.10 | 1.6 | 0.01 | 0.31 | 0.10 |
| Initial color tone (APHA) | 5 | 5 | 5 | 5 | 5 | 5 |
| Atmosphere of gas phase part | Air | Air | Air | Air | 7% oxygen/nitrogen | 7% oxygen/nitrogen |
| Water content (%) of gas phase part | 1.8 | 1.8 | 1.8 | 1.8 | 0.6 | 0.6 |
| Storing temperature (° C.) | 40 | 40 | 40 | 40 | 40 | 40 |
| Color tone after seven days (APHA) | 280 | 250 | 300 | 250 | 230 | 200 |

TABLE 3-continued

|  | Example 10 | Example 11 | Example 12 | Example 13 | Example 14 | Example 15 |
|---|---|---|---|---|---|---|
| Concentration of acrylic acid (ppm) | 630 | 600 | 610 | 650 | 430 | 450 |
| Precipitate | None | None | None | None | None | None |

TABLE 4

|  | Control | Control 2 | Control 3 | Referential Example 2 |
|---|---|---|---|---|
| Ra of test piece of SUS 304 | 2.11 | 6.43 | 2.11 | None of test piese (glass) |
| Initial color tone (APHA) | 5 | 5 | 5 | 5 |
| Atmosphere of gas phase part | Air | Air | 7% oxygen/ nitrogen | Air |
| Water content (%) of gas phase part | 1.8 | 1.8 | 0.6 | 1.8 |
| Storing temperature (° C.) | 40 | 40 | 40 | 40 |
| Color tone after seven days (APHA) | 450 | 450 | 400 | 250 |
| Concentration of acrylic acid (ppm) | 620 | 650 | 420 | 630 |
| Precipitate | None | None | None | None |

Example 16

In a 100 ml of well closed SUS 304 container, 100 ml in inner volume, 80 ml of dimethylaminoethyl acrylate (of the grade containing 1900 ppm of hydroquinone monomethyl ether; made by Nippon Shokubai K. K.) was placed and, with the gas phase part of the container displaced with a gas having a water content of 0.01 vol. % and a composition of 7 vol. % of molecular oxygen and 93 vol. % of nitrogen, stored therein at 20° C. When the dimethylaminoethyl acrylate was tested for acrylic acid concentration after three months' storage, the concentration was found to be 0.003 wt. %. In spite of the three months' storage, the dimethylaminoethyl acrylate showed no sign of either precipitate or coloration.

Example 17

The storage was performed by following the procedure of Example 16 while effecting the displacement of the gas phase part with air having a water content of 0.01 vol. %. When the dimethylaminoethyl acrylate was tested for acrylic acid concentration after three months' storage, the concentration was found to be 0.004 wt. %. In spite of the three months' storage, the dimethylaminoethyl acrylate showed no sign of either precipitate or coloration.

Example 18

The storage was performed by following the procedure of Example 16 while effecting the displacement of the gas phase part with air having a water content of 0.1 vol. %. When the dimethylaminoethyl acrylate was tested for acrylic acid concentration after two months' storage, the concentration was found to be 0.05 wt. %. In spite of the two months' storage, the dimethylaminoethyl acrylate showed no sign of either precipitate or coloration.

Example 19

The storage was performed by following the procedure of Example 16 while effecting the displacement of the gas phase part with a gas having a water content of 0.01 vol. % and a composition of 2 vol. % of oxygen and 98 vol. % of nitrogen. When the dimethylaminoethyl acrylate was tested for acrylic acid concentration after three months' storage, the concentration was found to be 0.003 wt. %. In spite of the three months' storage, the dimethylaminoethyl acrylate showed no sign of either precipitate or coloration.

Control 4

The storage was performed in a beaker by following the procedure of Example 16 while having the gas phase part open in a room kept at a temperature of 20° C. and a humidity of 65%. When the dimethylaminoethyl acrylate was tested for acrylic acid concentration after three days' storage, the concentration was found to be 0.3 wt. %.

The beaker was found to have formed adhesive matter on the bottom thereof after three days' storage.

Control 5

The storage was performed by following the procedure of Example 16 while having the gas phase part swept with a gas having a water content of 0.2 vol. % and a composition of 2 vol. % of oxygen and 98 vol. % of nitrogen. When the dimethylamino-ethyl acrylate was tested for acrylic acid concentration after one month's storage, the concentration was found to be 0.11 wt. %. The container was found to have formed a sediment after one month's storage.

The entire disclosure of Japanese Patent Application No.10-237355 filed on Aug. 24, 1998, Japanese Patent Application No.10-237356 filed on Aug. 24, 1998 and Japanese Patent Application No.11-226968 filed on Aug. 10, 1999 including specification, claims, drawing and summary are incorporated herein by reference in its entirety.

What is claimed is:

1. A method for handling an alkylaminoalkyl (meth) acrylate represented by the general formula (1)

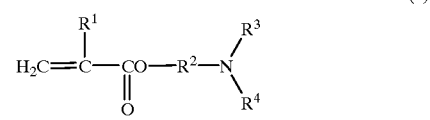

(1)

(wherein $R^1$ represents a hydrogen atom or a methyl group, $R^2$ an alkylene group of 1–4 carbon atoms, $R^3$ a hydrogen atom or an alkyl group of 1–8 carbon atoms, and $R^4$ an alkyl group of 1–8 carbon atoms) by keeping in contact with stainless steel, wherein said stainless steel contacting with said compound is not more than 1.6 μm for the Ra defined in JIS (Japanese Industrial Standard) B 0601.

2. A method for handling an alkylaminoalkyl (meth) acrylate represented by the general formula (1)

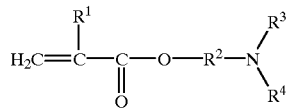

(1)

(wherein $R^1$ represents a hydrogen atom or a methyl group, $R^2$ an alkylene group of 1–4 carbon atoms, $R^3$ a hydrogen atom or an alkyl group of 1–8 carbon atoms, and $R^4$ an alkyl group of 1–8 carbon atoms), comprising contacting the alkylaminoalkyl (meth)acrylate with stainless steel, wherein the concentration of water is not more than 0.1% based on the volume of the gas phase part contacting with said alkylaminoalkyl (meth)acrylate and the concentration of (meth)acrylic acid is not more than 0.1% based on the weight of said alkylaminoalkyl (meth)acrylate.

3. A method according to claim 1, wherein the concentration of oxygen of the gas phase part contacting with said alkylaminoalkyl (meth)acrylate is in the range of 0 to 10 vol. %.

4. A method according to claim 1, wherein the temperature of handling is not higher than 40° C.

5. A method for preventing alkylaminoalkyl (meth) acrylate represented by the general formula (1)

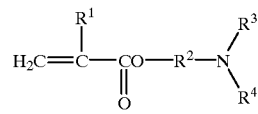

(1)

(wherein $R^1$ represents a hydrogen atom or a methyl group, $R^2$ an alkylene group of 1–4 carbon atoms, $R^3$ a hydrogen atom or an alkyl group of 1–8 carbon atoms, and $R^4$ an alkyl group of 1–8 carbon atoms) from coloration by keeping in contact with stainless steel, wherein said stainless steel contacting with said compound is not more than 1.6 μm for the Ra defined in JIS (Japanese Industrial Standard) B 0601.

6. A method for preventing coloration of alkylaminoalkyl acrylate represented by the general formula (1)

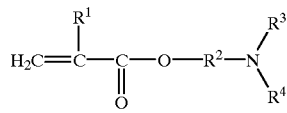

(1)

(wherein $R^1$ represents a hydrogen atom or a methyl group, $R^2$ an alkylene group of 1–4 carbon atoms, $R^3$ a hydrogen atom or an alkyl group of 1–8 carbon atoms, and $R^4$ an alkyl group of 1–8 carbon atoms), comprising contacting the alkylaminoalkyl (meth)acrylate with stainless steel, wherein the concentration of water is not more than 0.1% based on the volume of the gas phase part contacting with said alkylaminoalkyl (meth)acrylate and the concentration of (meth)acrylic acid is not more than 0.1% based on the weight of said alkylaminoalkyl (meth)acrylate.

7. A method according to claim 5, wherein the concentration of oxygen of the gas phase part contacting with said alkylaminoalkyl (meth)acrylate is in the range of 0 to 10 vol. %.

8. A method according claim 5, wherein the temperature of handling is not higher than 40° C.

9. An apparatus to use for the method according to claim 1, which comprises a container made of stainless steel whose wall surface contacting with said compound is not more than 1.6 μm for the Ra defined in JIS B 0601 and means for retaining the water content in the gas phase part of a storage container below 0.1 vol. %.

10. An apparatus according to claim 9, which further comprises means for adjusting the gas phase part of said storage container to have an oxygen concentration in the range of 0 to 10 vol. %.

11. A method according to claim 2 wherein the concentration of oxygen of the gas phase part contacting with said alkylaminoalkyl (meth)acrylate is in the range of 0 to 10 vol. %.

12. A method according to claim 2 wherein the temperature of handling is not higher than 40° C.

13. A method according to claim 3 wherein the temperature of handling is not higher than 40° C.

14. A method according to claim 11 wherein the temperature of handling is not higher than 40° C.

15. A method according to claim 6 wherein the concentration of oxygen of the gas phase part contacting with said alkylaminoalkyl (meth)acrylate is in the range of 0 to 10 vol. %.

16. A method according to claim 6 wherein the temperature of handling is not higher than 40° C.

17. A method according to claim 7 wherein the temperature of handling is not higher than 40° C.

18. A method according to claim 15 wherein the temperature of handling is not higher than 40° C.

* * * * *